(12) United States Patent
Hutchenson et al.

(10) Patent No.: US 8,293,217 B2
(45) Date of Patent: Oct. 23, 2012

(54) HYDROGENATION OF CARYOPHELLENE

(75) Inventors: Keith W. Hutchenson, Lincoln University, PA (US); Scott Christopher Jackson, Wilmington, DE (US); Leo Ernest Manzer, Wilmington, DE (US); Mark A. Scialdone, West Grove, PA (US); Mayis Seapan, Landenberg, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 287 days.

(21) Appl. No.: 12/519,614

(22) PCT Filed: Dec. 20, 2007

(86) PCT No.: PCT/US2007/025983
§ 371 (c)(1),
(2), (4) Date: Jun. 17, 2009

(87) PCT Pub. No.: WO2008/079250
PCT Pub. Date: Jul. 3, 2008

(65) Prior Publication Data
US 2010/0092404 A1   Apr. 15, 2010

Related U.S. Application Data

(60) Provisional application No. 60/876,555, filed on Dec. 21, 2006.

(51) Int. Cl.
*A61K 8/31* (2006.01)
*A61K 8/33* (2006.01)
*A61Q 17/04* (2006.01)
*A61Q 17/02* (2006.01)
*A01N 33/00* (2006.01)
*A01N 27/00* (2006.01)
*A01N 31/02* (2006.01)

(52) U.S. Cl. ......... 424/59; 424/76.2; 514/729; 514/763; 514/766

(58) Field of Classification Search ........................ None
See application file for complete search history.

(56) References Cited

U.S. PATENT DOCUMENTS

| | | | |
|---|---|---|---|
| 3,966,819 A | 6/1976 | Schulte-Elte et al. | |
| 6,359,000 B1 | 3/2002 | Jiang | |
| 7,067,677 B2 | 6/2006 | Manzer | |
| 2003/0062357 A1 | 4/2003 | Schneider et al. | |
| 2003/0079786 A1 | 5/2003 | Diana et al. | |
| 2003/0191047 A1 | 10/2003 | Hallahan | |
| 2004/0191342 A1* | 9/2004 | Pichette et al. | ............... 424/769 |
| 2006/0148842 A1 | 7/2006 | Scialdone | |
| 2007/0264297 A1 | 11/2007 | Scialdone | |
| 2010/0145077 A1 | 6/2010 | Jackson | |
| 2010/0145078 A1 | 6/2010 | Fisher | |
| 2010/0168447 A1 | 7/2010 | Hutchenson | |

OTHER PUBLICATIONS

Sorm et al., Chemical Proof of the Carbon Skelton of Caryophyllene, Chemistry and Industry, 1956, pp. 154-155.
Regnier et al., Nepetalactone and Epinepetalactone From *Nepeta cataria* L., Phytochemistry, 1967, vol. 6, pp. 1271 to 1280.
Rao, Hydroboration and Dimide Reduction of Caryophyllene and Isocaryophyllene, Tetrahedron, 1978, vol. 34, pp. 2223 to 2227.
International Search Report, PCT/US2007/025983, Dated Jul. 11, 2008.
Naves et al., Studies on the Volatile Vegetable Materials, XIV, The Structure of Caryophyllene, Helvetica Chimica, 1941, vol. 16, pp. 789-804.
Regnier, Waller and Eisenbraun: Studies on the Composition of the Essential Oils of Three Nepeta Species: Phytochemistry, 1967, vol. 6, pp. 1281-1289; Pergamon Press, New York.
DePooter, Nicolai, DeLaet, DeBuyck and Schamp; The Essential Oils of Five Nepeta Species, A Preliminary Evaluation of Their Use in Chemotaxonomy by Cluster Analysis: Flavour and Fragrance Journal, vol. 3, pp. 155-159 (1988): John Wiley & Sons, New York.
Handjieva and Popov; Constituents of Essential Oils from Nepeta Cataria L., Grandiflora M.B. and N. Nuda L.; Journal of Essential Oil Research, vol. 8, pp. 639-643 (Nov./Dec. 1996); Allured Publishing Corp., New York.

* cited by examiner

*Primary Examiner* — Ernst Arnold

(57) ABSTRACT

A process for the hydrogenation of a mixture of caryophyllenes by contact with hydrogen in the presence of a supported catalyst. The resulting products are useful for the application to skin.

7 Claims, 1 Drawing Sheet

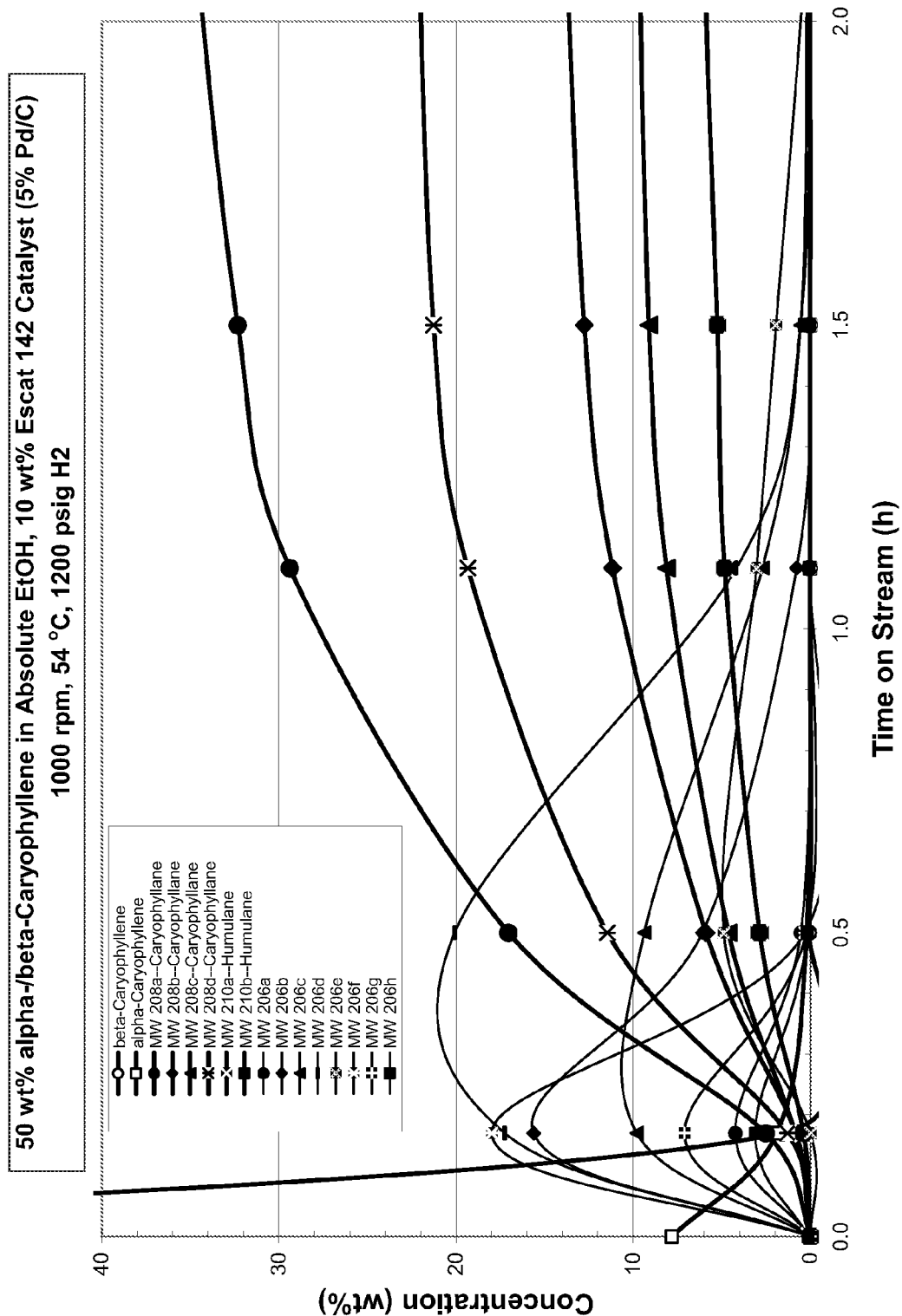

HYDROGENATION OF CARYOPHELLENE

This application claims the benefit of U.S. Provisional Application No. 60/876,555, filed 21 Dec. 2006, which is incorporated in its entirety as a part hereof for all purposes.

TECHNICAL FIELD

This invention relates to a process for hydrogenating caryophyllenes. Mixtures comprising hydrogenated caryophyllene are useful for the purpose of providing enhancements to skin.

BACKGROUND

Caryophyllene is a sesquiterpenoid derivative that can be obtained from the oils of a number of plants, such as clove and catmint.

The partial reduction of caryophyllene, or isomers thereof, to their corresponding dihydro forms has been disclosed in several references. U.S. Pat. No. 3,966,819 discloses the photoisomerization of caryophyllene to iso-caryophyllene, and discloses that iso-caryophyllene can be hydrogenated to iso-dihydrocaryophyllene in the presence of a Raney nickel catalyst. Rao and Devaprabhakara [*Tetrahedron* (1978) 34:2223-2227] describe the partial reduction of caryophyllene and isocaryophyllene with diimide to the dihydro products dihydrocaryophyllene and dihydroisocaryophyllene, respectively.

Several references describe the complete hydrogenation of caryophyllene to the tetrahydro derivative. Naves and Perrottet ["Volatile Plant Materials, XIV, Structure of Caryophyllene", *Helv. Chim. Acta*, (1941) 24:789-804] disclose the hydrogenation of caryophyllene to tetrahydrocaryophyllene in the presence of $PtO_2$, which is an unsupported catalyst. Similarly, Sorm et al [*Chemistry & Industry* (1956) 154-155] disclose the preparation of tetrahydrocaryophyllene by catalytic hydrogenation of caryophyllene with $PtO_2$ in the presence of glacial acetic acid.

A need nevertheless exists for an economically viable route to the synthesis of the hydrogenated forms of caryophyllene.

SUMMARY

One embodiment of this invention involves a process for preparing a reaction product comprising at least one member of the group consisting of dihydro-β-caryophyllene, α-humulane and β-caryophyllane; by
(a) contacting a mixture comprising α-humulene and β-caryophyllene with hydrogen in the presence of at least one supported catalyst to form the reaction product; and
(b) optionally, separating the reaction product from the supported catalyst.

The catalytic metals useful for the process include those that may be selected from elements in group consisting of iron, ruthenium, rhenium, copper, osmium, cobalt, rhodium, iridium, nickel, palladium, platinum, and alloys or compounds thereof. A support for the catalytic metal includes those that may be selected from the group consisting of carbon, alumina, silica, silica-alumina, silica-titania, titania, titania-alumina, barium sulfate, calcium carbonate, strontium carbonate, compounds thereof, and combinations thereof. The weight of the catalytic metal in the supported catalyst typically constitutes from about 0.1% to about 70% of the combined weight of the catalytic metal plus the support.

The reaction may be run at a temperature in the range of from about 0° C. to about 200° C. Hydrogen may be fed at a pressure in the range of from about 0.1 MPa to about 20.7 MPa. Solvents useful for the reaction include without limitation ethanol, isopropanol, hexane, cyclohexane, ethyl acetate, dioxane, tetrahydrofuran and diethyl ether.

Another embodiment of the processes hereof involves a process wherein there is an additional step of incorporating the reaction product info a composition of matter that contains, in addition to the reaction product, a carrier and/or a cosmetically-active adjuvant.

A further embodiment of this invention involves a composition of matter (such as a topical treatment for skin) or an article of manufacture that includes at least one member of the group consisting of dihydro-β-caryophyllene, α-humulane and β-caryophyllane. Such a composition may also contain a carrier, a cosmetically-active adjuvant, and/or a dihydronepetalactone.

Yet another embodiment of this invention involves a method for imparting fragrance to, or revitalizing, the skin, hide, hair, fur, feathers or other surface of a human or a domesticated animal by applying thereto a composition of matter that contains (a) at least one member of the group consisting of dihydro-β-caryophyllene, α-humulane and β-caryophyllane; and (b) a carrier and/or a cosmetically-active adjuvant.

The compositions of this invention are useful for the purpose of imparting a fragrance to, or otherwise enhancing or revitalizing, the skin, hide, hair, fur, feathers or other surface of a human or a domesticated, companion or sporting animal, such as a dog, cat or horse.

BRIEF DESCRIPTION OF THE DRAWING

FIG. 1 shows the hydrogenation over time of caryophyllene isomers and the hydrogenated isomers thereof.

DETAILED DESCRIPTION

This invention provides a process for the hydrogenation of a mixture comprising alpha- and beta-caryophyllene in the presence of a supported catalyst, as well as the reaction-product compounds obtained from such process, and compositions prepared from those compounds.

DEFINITIONS

In the description of the inventions hereof, the following definitional structure is provided for certain terminology as employed in various locations in the specification:

The term "beta-caryophyllene" or "β-caryophyllene" or "(1R,4E,9S)-4,11,11-trimethyl-8-methylene-bicyclo[7.2.0]undec-4-ene", as used herein, refers to the compound having the structural formula [Molecular Weight (MW) 204]:

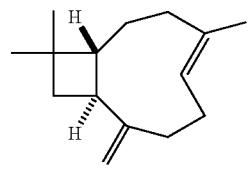

The term "dihydro-β-caryophyllene" or "4,8,11,11-tetramethyl-bicyclo[7.2.0]undec-4-ene", as used herein, refers to a single isomer or a mixture of isomers having the 8R and/or 8S isomeric configuration shown below, wherein the 8R isomer is (1R,4E,8R,9R)-4,8,11,11-tetramethylbicyclo[7,2,0]undec-4-ene and the 8S isomer is (1R,4E,8S,9R)-4,8,11,11-tetramethylbicyclo[7.2.0]undec-4-ene (MW 206):

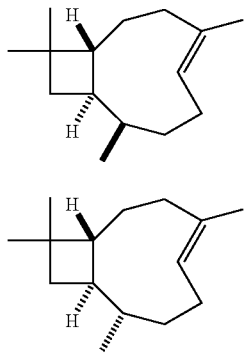

The term "alpha-humulene" or "α-humulene" or "alpha-caryophyllene" or "(1E,4E,8E)-2,6,6,9-tetramethyl-1,4,8-cycloundecatriene", as used herein, refers to the compound having the structural formula (MW 204):

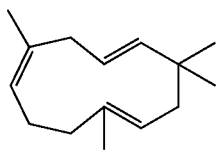

The term "beta-caryophyllane" or "β-caryophyllane" or "2,6,10,10-tetramethyl-bicyclo[7.2.0]undecane", as used herein, refers to a single isomer or a mixture of isomers having the (i) 2R,6R, (ii) 2R,6S, (iii) 2S,6S and/or (iv) 2S,6R isomeric configuration shown below, wherein the 2R,6R isomer is (1R,2R,6R,9R)-2,6,10,10-tetramethylbicyclo[7.2.0]undecane, the 2R,6S isomer is (1R,2R,6S,9R)-2,6,10,10-tetramethylbicyclo[7.2.0]undecane, the 2S,6S isomer is (1R,2S,6S,9R)-2,6,10,10-tetramethylbicyclo[7.2.0]undecane, and the 2S,6R isomer is (1R,2S,6R,9R)-2,6,10,10-tetramethylbicyclo[7.2.0]undecane (MW 208):

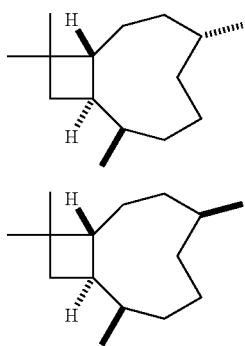

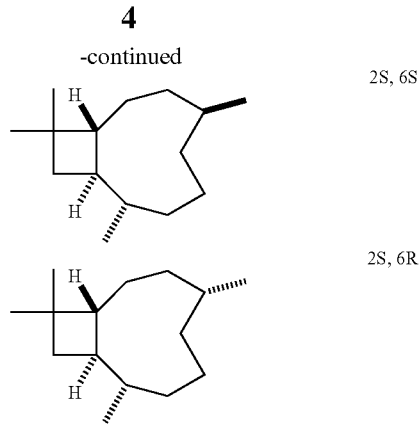

The term "alpha-humulane" or "α-humulane" or "1,1,4,8-tetramethyl-(6CI,8CI,9CI)cycloundecane", as used herein, refers to a single isomer or a mixture of isomers having the (i) 4R,8R, (ii) 4R,8S, (iii) 4S,8S and/or (iv) 4S,8R isomeric configuration shown below, wherein the 4R,8R isomer is (4R,8R)-1,1,4,8-tetramethylcycloundecane, the 4R,8S isomer is (4R,8S)-1,1,4,8-tetramethylcycloundecane, the 4S,8S isomer is (4S,8S)-1,1,4,8-tetramethylcycloundecane, and the 4S,8R isomer is (4S,8R)-1,1,4,8-tetramethylcycloundecane (MW 210);

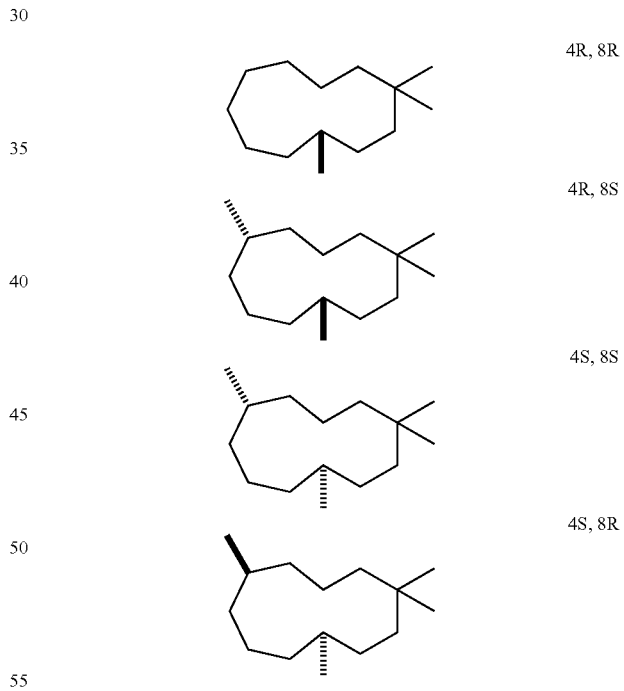

A "catalyst" is a substance that affects the rate of the reaction but not the reaction equilibrium, and emerges from the process chemically unchanged.

More specifically, this invention provides a process for preparing a reaction product comprising at least one member of the group consisting of dihydro-β-caryophyllene, α-humulane and β-caryophyllane; by (a) contacting a mixture comprising α-humulene and β-caryophyllene with hydrogen in the presence of at least one supported catalyst to form the reaction product; and (b) optionally, separating the reaction product from the supported catalyst.

According to the processes hereof, the mixture comprising α-humulene and β-caryophyllene can be partially reduced, wherein one or more of the double bonds of the caryophyllene isomers are hydrogenated, or the mixture may be completely reduced, such that all of the double bonds are hydrogenated. A scheme depicting several possible reaction sequences for the partial and complete hydrogenation of caryophyllenes is shown below:

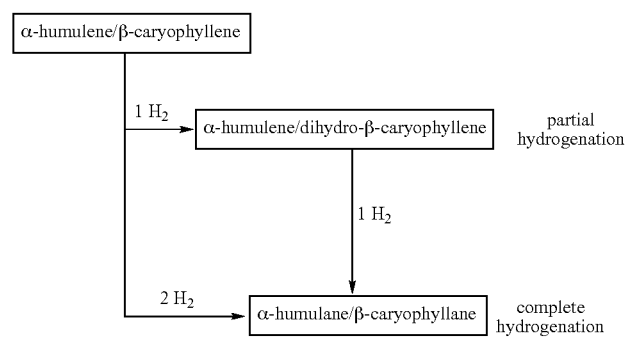

In various embodiments, it may be found that the exocylic methylene group of beta-caryophyllene is hydrogenated more readily than the endocyclic double bonds of α-humulene or β-caryophyllene.

Caryophyllenes useful as starting materials in the reaction may be obtained commercially from a supplier such as Sigma-Aldrich (St. Louis Mo.). Caryophyllenes are sesquiterpenoids found in the essential oils of many plants, such as clove and catmint; the essential oils may be obtained from plant sources by known methods, including steam, distillation such as described in Regnier et al [*Phytochem.* (1967) 6; 1271-1280].

A supported catalyst, as used herein, at least one catalytic metal on a support. The catalytic metal is deposited on the support by any one of a number of methods, such as spraying, seating or physical mixing, followed by drying, calcination, and if necessary, activation through methods such as reduction or oxidation/reduction. A supported catalyst may also be made by co-precipitation or bleeding of the active components and the support followed by drying, calcination, and if necessary, activation through methods such as reduction or oxidation/reduction. Materials frequently used as a catalyst support are porous solids with high total surface areas (external and internal) which can provide high concentrations of active sites per unit weight of catalyst.

In the processes hereof, supported catalysts are preferred to unsupported catalysts for a variety of reasons. The support allows greater efficiency in the use of the metal by increasing the active metal surface and by facilitating metal recovery. Supported catalysts generally have a greater resistance to poisoning. In addition, the support provides for better control over selectivity.

The catalytic metal may be selected from elements in the group consisting of iron, ruthenium, rhenium, copper, osmium, cobalt, rhodium, iridium, nickel, palladium, platinum, alloys or compounds thereof, and combinations thereof. In a more specific embodiment, the catalytic metal may be selected from elements in the group consisting of palladium, rhodium, iridium, alloys or compounds thereof, and combinations thereof. The catalytic metal may, however, be selected from any subgroup of the foregoing list formed by omitting other members of the list to leave only the members of the subgroup, and the reaction in such instance is run in the absence of the members of the list omitted to form the subgroup.

A support for the supported catalyst may be selected from the group consisting of carbon, alumina, silica, silica-alumina, silica-titania, titania, titania-alumina, barium sulfate, calcium carbonate, strontium carbonate, compounds thereof, and combinations thereof. In a more specific embodiment, the support may be selected from the group consisting of carbon, alumina, silica, silica-alumina, compounds thereof, and combinations thereof. In an even more specific embodiment, the support material may be carbon with a surface area greater than 100 $m^2/g$, or carbon with a surface area greater than 200 $m^2/g$. Preferably, the carbon has an ash content that is less than 5% by weight of the catalyst support; the ash content is the inorganic residue (expressed as a percentage of the original weight of the carbon) which remains after incineration of the carbon.

Commercially available carbons which may be used herein as a support include those sold under the following trademarks: Bameby & Sutcliffe™, Darco™, Nuchar™, Columbia JXN™, Columbia LCK™, Calgon PCB™, Calgon BPL™, Westvaco™, Norit™ and Bamaby Cheny NB™. The carbon can also be commercially available carbon such as Calsicat C, Sibunit C, or Calgon C (commercially available under the registered trademark Centaur®).

The catalyst support can be in the form of powder, granules, pellets, extrudates, or the like.

In the process hereof, the content of the catalytic metal in a supported catalyst will depend on the choice of the catalyst and support. In one embodiment, the content of the catalytic metal in the supported catalyst may be from about 0.1% to about 10% of the supported catalyst based on catalytic metal weight plus the support weight.

Promoter metals may be used to enhance the physical or chemical function of a catalyst. Promoter metals are often selected from metals from Groups 3 through 8, 11 and 12 of the Periodic Table, and are typically used at up to about 2% by weight of the total metal of the promoter plus the catalytic metal. Promoter metals may be used to enhance the activity of the supported catalyst useful for the present invention.

Combinations of catalytic metal and support useful herein include at least one catalytic metal as described above with at least one support as described above. In a more specific embodiment, combinations of catalytic metal and support may be selected from the group consisting of palladium on carbon, palladium on alumina, palladium on silica, palladium on silica-alumina, rhodium on carbon, rhodium on alumina, rhodium on silica, rhodium on silica-alumina, iridium on carbon, iridium on alumina, iridium on silica, iridium on silica-alumina, and combinations thereof.

The reaction may be run at a temperature in the range of from about 0° C. to about 200° C. In a more specific embodiment, the reaction may be run at a temperature in the range of from about 25° C. to about 150° C. In an even more specific embodiment, the reaction may be run at a temperature of from about 50° C. to about 100° C.

The hydrogen feed useful for the reaction may be supplied at a pressure in the range of from about 0.1 MPa to about 20.7 MPa. In one embodiment, the hydrogen is maintained at a pressure to achieve saturation levels of the hydrogen in the mixture at the temperature of the reaction.

Solvents may be used in the processes hereof, if desired, and when used are typically inert solvents. Suitable solvents may include without limitation alcohols such as ethanol or isopropanol; alkanes such as hexane or cyolohexane; esters such as ethyl acetate; and ethers such as dioxane, tetrahydrofuran or diethyl ether.

The reaction product comprising the hydrogenated caryophyllenes may be separated from the at least one supported catalyst by any suitable method, such as decantation. For those reactions in which a solvent is used, the reaction product comprising the hydrogenated caryophyllenes may additionally comprise the solvent, or alternatively, the solvent may be recovered from the reaction product using standard techniques known to those skilled in the art, such as distillation or vacuum stripping.

The processes hereof may be carried out in batch in a single reactor, in sequential batch in a series of reactors, in reaction zones within one or more reactors, or in continuous mode in any or the equipment customarily employed for continuous processes.

The reaction products will be determined by the conditions under which the reaction is carried out inasmuch as temperature, hydrogen pressure, catalytic metal, support and time can affect the reaction kinetics, product yield and product selectivity. For example, with a given supported catalyst at a given pressure, β-caryophyllene may be hydrogenated to dihydro-β-caryophyllene at 50° C., whereas α-humulene is not hydrogenated. Under the same conditions except using a temperature of 100° C., both β-caryophyllene and α-humulene may be completely hydrogenated to β-caryophyllane and α-humulane, respectively. The conditions required for producing a specified mixture of products may be similarly determined.

This invention relates to the Hydrogenation Reaction Products ("HRP") as described above (dihydro-β-caryophyllene, α-humulane and/or β-caryophyllane), to compositions comprising HRP, and to the use of HRP and the compositions thereof. The preparations of this invention, which include the HRP compounds described above, and the compositions, formulations and other materials that may be prepared from such compounds according to this invention, and mixtures thereof, may all be used for a multiplicity of purposes. These purposes include, for example, use as a fragrance compound itself or as an ingredient in a perfume composition, or use as a topical treatment for skin.

For example, the preparations hereof may be applied in a topical manner to the skin, hide, hair, fur, feathers or other surface of a mammal, such as a human or domesticated animal.

The preparations hereof may also be applied to the skin and/or hair of humans to impart a pleasant odor or aroma as a fragrance compound itself, or as an ingredient in a perfume composition; and the preparations hereof may also be used as a topical treatment for skin by application to the skin and/or hair of humans in the form of a body wash, rinse, conditioner, toner, lotion, splash, spray or other type of cosmetic product as applied personally by the user.

Alternatively, the active ingredient may be contained in microcapsules to control the rate of loss from a surface or an article; a precursor molecule, which slowly disintegrates on a surface or in an article, may be used to control the rate of release of the active ingredient; or a synergist may be used to continually stimulate the evaporation of the active from the formulated composition.

The release of an active ingredient that is intended for application to the skin or other surface of a user may be accomplished, for example, by sub-micron encapsulation, in which the active ingredient is encapsulated or enveloped in a skin-nourishing protein. The protein may be used, for example, at about a 20 wt % concentration. An application of repellent contains many of these protein capsules that may be suspended in either a water-based lotion, or water for spray application. After contact with shin, the protein capsules begin to break down, releasing the encapsulated active. The process continues as each microscopic capsule is depleted then replaced in succession by a new capsule that contacts the surface and releases its active ingredient. The process may take up to 24 hours for one application. Because a protein adheres very effectively to skin, these formulations are very resistant to perspiration (sweat-off) and dilution by water from other sources.

One of the distinct advantages of the preparations of this invention is that they are all characterized by a relative volatility that makes them suitable for use to obtain a desirably high level of concentration of active ingredient on, above and around a surface of a user, as described above. One or more of these preparations may be used for such purpose as an active, or an active formulation, in a composition in which the preparation is admixed with a carrier suitable for wet or dry application of the composition to a surface in the form, for example, of a liquid, aerosol, gel, aerogel, foam or powder (such as a sprayable powder or a dusting powder). Suitable carriers include any one of a variety of commercially available organic and inorganic liquid, solid, or semi-solid carriers or carrier formulations usable in formulating a variety of cosmetic products. When formulating a composition for application to the skin or other surface of a human, if is important to select a dermatologically acceptable carrier. A carrier suitable for use herein may include water, alcohol, silicone, petrolatum, lanolin; or may include an organic liquid carrier such as a liquid aliphatic hydrocarbon (e.g. pentane, hexane, heptane, nonane, decane and their analogs) or a liquid aromatic hydrocarbon.

Examples of other useful liquid hydrocarbons include oils produced by the distillation of coal and the distillation of various types and grades of petrochemical stocks, including kerosene oils that are obtained by fractional distillation of petroleum. Suitable petroleum oils include those generally referred to as agricultural spray oils (e.g. the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other suitable carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials. In addition to the above-mentioned liquid hydrocarbons, the carrier can contain conventional emulsifying agents which can be used for causing the active ingredient to be dispersed in, and diluted with, water for end-use application. Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g. tert-butyl sulfinyl dimethyl dithiocarbonate) can be used in conjunction with, or as a component of, the carrier or carriers used in a composition as made according to this invention.

Numerous clays having a layered structure with interstices, and synthetic inorganic materials that resemble such clays in respect of chemical composition, crystallinity and layered morphology, are suitable for use herein as carriers. Suitable clays having a layered structure with interstices include smectite, kaolin, muscovite, vermiculite, phlogopite, xanthophyllite, and chrysotile, and mixtures thereof. Preferred are smectite clays and kaolin clays. Smectite clays include montmorillonite, beidellite, nontronite, saponite, hectorite, sauconite, and others. Kaolin clays include kaolinite, deckite, nacrite, antigorite, and others. Most preferred is montmorillonite. Average particle sizes range from 0.5 to 50 micrometers.

The application of a preparation hereof may be accomplished by dispersing the preparation into the air, or by dispersing the preparation as a liquid mist or incorporated into a powder or dust, and this will permit the composition to fall on the desired surfaces of a user. It may also be desirable to combine a preparation hereof with a fugitive vehicle for application in the form of a spray. Such a composition may be an aerosol, sprayable liquid or sprayable powder composition adapted to disperse the active ingredient into the atmosphere by means of a compressed gas, or a mechanical pump spray. Likewise, directly spreading a preparation in liquid/semi-solid/solid form on a user in wet or dry form (as a friable solid, for example) is a useful method of contacting a surface of the user.

Further, it may also be desirable to combine a preparation hereof with one or more other compounds known to have insect repellency in a composition. Suitable insect repellent compounds combinable for such purpose include nepetalactones, nepetalactams, dihydronepetalactones and derivatives thereof, dihydronepetalactams and derivatives thereof, benzil, benzyl benzoate, 2,3,4,5-bis(butyl-2-ene)tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normal-propyl isocinchomeronate, 2-phenylcyclohexanol, p-methane-3,8-diol, and normal-propyl N,N-diethylsuccinamate.

Suitable dihydronepetalactones for use as a component in a composition hereof include: the 9S dihydronepetalactones as shown below:

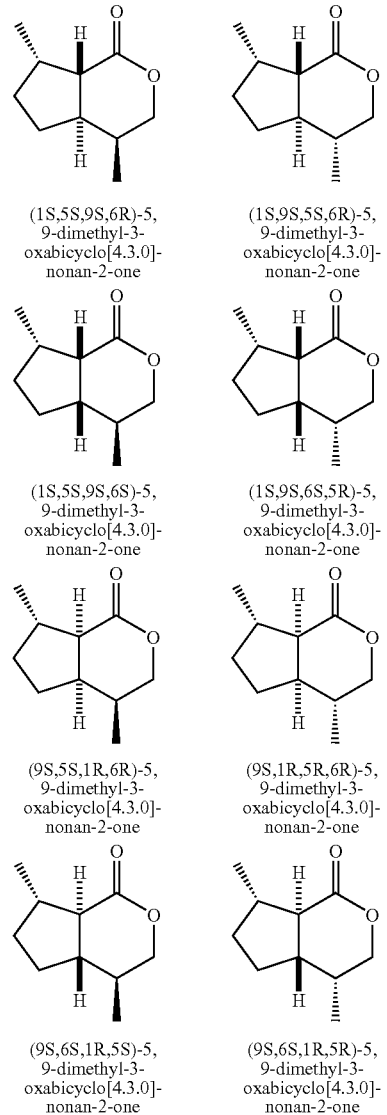

In addition, a preparations hereof may also include one or more essential oils and/or active ingredients of essential oils. An essential oil includes any type of volatile oil that is obtained from a plant and possesses the odor and other characteristic properties of the plant. Examples of useful essential oils include: almond, bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

In another embodiment, a preparation hereof may be used as a fragrance material or as an active in a fragrance composition, and be applied in a topical manner to human or animal skin or hair to impart a pleasing scent or aroma thereto, as in colognes or perfumes for humans or pets. Alternatively, the pleasing scent or aroma may be obtained by the use of a preparation hereof as an insect/arthropod repellent where the preparation has the dual attributes of simultaneously imparting both repellency as well as the pleasing scent or aroma.

As used herein, the terms "alter" and "modify" in their various forms refer to a means of supplying or imparting a fragrance, aroma character or note to otherwise bland substances, or augmenting existing aroma characteristics where natural aroma is deficient in some regard, or supplementing an existing aroma impression to modify its quality, character, or aroma.

The term "enhance" is intended to mean the intensification (without effecting a change in kind or quality of aroma) of one or more aroma nuances and their organoleptic impression of a fragrance, perfume composition, or one or more perfumed articles.

The term "fragrance note(s)" or "note(s)" refers to the three stages that most fragrances go through. The top note is the first impression of the fragrance. The middle note is the main character of a fragrance. These are stronger, mid-range notes that emerge after the top and linger longest, as the 'heart' of the fragrance. Finally, the base note is the final scent of the fragrance. These rich, heavy notes emerge slowly and definitely, echoing resonantly after the others die down. Bottom notes, by definition, linger behind and act as a fixative to stop the lighter oils from dispersing too quickly.

The terms "perfume composition" or "fragrance composition" or "aroma composition" are used herein to mean a mixture of organic compounds including, for example, alcohols, aldehydes, ketones, nitrides, esters, lactones, natural essential oils, synthetic essential oils, and mercaptans, which are admixed so that the combined odors of the individual components produce a pleasant or desired fragrance. Such compositions usually contain: (1) the main note or the "bouquet" or foundation stone of the composition; (2) modifiers which round off and accompany the main note; (3) fixatives which include odorous substances which lend a particular note to the perfume throughout all stages of evaporation and substances which retard evaporation; and (4) top notes which are usually low-boiling, fresh-smelling materials.

A perfume is characterized by its uniquely pleasing fragrance or aroma. In perfume, fragrance or aroma compositions, the individual component will contribute its particular olfactory characteristics, but the overall effect of the composition will be the sum of each of the effects of each of the ingredients. Thus, an HRP can be used to alter the aroma characteristics of such compositions, for example, by highlighting or moderating the olfactory reaction contributed by another ingredient in the composition.

A "perfume composition" may contain a perfume compound, a fragrance compound or an aroma compound in addition to other materials. Moreover, a "perfume composition" or "fragrance composition" can be used as components of an article such as a "perfumed article" or "fragrant article", or the composition may be added to perfumed or fragrant articles, wherein the term "perfumed article" or "fragrant article" refers to an article of manufacture possessing a pleasing fragrance or aroma, or a fragrance or aroma that is enhanced, altered, or augmented by the perfume composition.

The unique fragrance notes of an HRP thus make them useful in impacting, altering, augmenting or enhancing the overall olfactory component of a perfume composition, for example, by utilizing or moderating the olfactory reaction contributed by one or more other ingredients in the composition. Specifically, the composition may be utilized to either: (1) impact a characteristic perfume or aroma to a perfume or article; or (2) mask or modify the odor of one or more of the components thereof.

As will be appreciated, fragrant materials are typically utilized in combinations that may include both natural and synthetic ingredients to achieve the desired overall perfume effect. Fragrance developers consider the scent of the compound, as well as its efficacy, degree of stability within the final formulation, activity during a product's shelf life, and lack of adverse reaction with the product or its intended function as a perfumed article. Typically, fragrances are used to mask the odor contributed by other ingredients in the formulation of the final scented product, and/or to enhance consumer appeal of a product.

An HRP possesses unique fragrant notes and, therefore, are particularly useful individually and in combination with other fragrant chemicals in a variety of perfume compositions. The overall effect of the perfume composition will be the sum of the effects of each of the ingredients. Thus, an HRP as used herein or mixtures thereof with other perfumery materials can be used to alter the aroma characteristics of a perfume composition, for example, by highlighting or moderating the olfactory reaction contributed by another ingredient in the preparation, such as a fragrance compound that is not an HRP. The HRPs according to the present invention can be used in practically every field of modern perfumery. Embodiments of the invention therefore are suitable for applications in fine perfumery, i.e. in the preparations of perfumes and colognes in which new and original effects can be obtained.

In a further embodiment, the insect/arthropod repellency, fragrance and/or other properties of products directed to other fundamental purposes will be improved by the presence therein of a preparation of this invention. Those other products include, for example, a body wash, rinse, lotion, splash, tonic or toner, bath and shower gels, foam products (e.g. shaving foams), makeup, deodorants, shampoo, hair lacquers/hair rinses, personal soap compositions (e.g. hand soaps and bath/shower soaps) or other personal care treatments or palliatives, and cleaning agents such as detergents and solvents, and air fresheners and odor removers. Such products may be fabricated, for example, in the form of a sprayable liquid, an aerosol, a foam, a cream, an ointment, a gel, a paste, a powder or a friable solid. The process of fabricating such a product would thus include admixing a preparation hereof with suitable carriers or other inert ingredients to facilitate delivery in the physical form as described, such as liquid carriers that are readily sprayed; a propellant for an aerosol or a roars; viscous carriers for a cream, an ointment, a gel or a paste; or dry or semi-solid carriers for a powder or a friable solid.

Any of the above described products may also contain other therapeutically or cosmetically active adjuvants or supplemental ingredients as are typical in the personal care industry. Examples of these include fungicides, sunscreening agents, sunblocking agents, vitamins, tanning agents, plant extracts, anti-inflammatory agents, antioxidants, radical scavenging agents, retinoids, alpha-hydroxy acids, antiseptics, antibiotics, antibacterial agents, antihistamines; adjuvants such as thickeners, buffering agents, chelating agents, preservatives, gelling agents, stabilizers, surfactants, emolients, coloring agents, aloe vera, waxes, and penetration enhancers; and mixtures of any two or more thereof.

Articles into which a preparation hereof may be incorporated to impart an improved fragrance include articles or manufactured goods such as textile and fibrous goods, clothing, sanitary goods, carpeting, linens, outdoor or military equipment such as tents, tarpaulins, backpacks or mosquito netting, candles, paper, paint, ink, wood products such as furniture, plastics and other polymers, and the like.

A preparation hereof may be formulated as or incorporated into a composition for application to an animate host by any of the same methods known in the cosmetics industry, such as dilution, mixing, thickening, emulsifying, bottling and pressurizing. A preparation hereof may be incorporated info an article by mixing during production or by post-production steps such as spraying or dipping.

A preparation hereof may be admixed in a composition, with other components, such as a carrier, in an amount that is effective for usage for a particular purpose. The amount of a HRP as described herein, contained in a composition will generally not exceed about 80% by weight based on the weight of the final product, however, greater amounts may be utilized in certain applications, and this amount is not limiting. Here preferably, a suitable amount of a HRP will be at least about 0.001% by weight and preferably about 0.01% up to about 50% by weight; and more preferably, from about 0.01% to about 20% weight percent, based on the total weight of the total composition or article. Specific compositions will depend on the intended use.

Other compositions, materials and methods relevant to the use of a HRP are as disclosed in US 2003/062,357; US 2003/079,786; US 2003/191,047; and US 2006/148,842, each of which is incorporated in its entirety as a part hereof for all purposes.

The advantageous attributes and effects of the processes hereof may be seen in a series of examples, as described below. The embodiments of these processes on which the examples are based are representative only, and the selection of those embodiments to illustrate the invention does not indicate that materials, conditions, arrangements, components, reactants, techniques or configurations not described in these examples are not suitable for practicing these processes, or that subject matter not described in these examples is excluded from the scope of the appended claims and equivalents thereof.

EXAMPLES

The following abbreviations are used in the examples: GC is gas chromatograph(y); GC-MS is gas chromatography-mass spectrometry; NMR is nuclear magnetic resonance; C is Centrigrade, MPa is mega Pascal; rpm is revolutions per minute; mL is milliliter; MW is molecular weight; CMO is catmint oil; wt % is weight percent; TOS is time on stream; h is hour; conc. is concentration; conv. is conversion; temp. is temperature; ° C. is degrees Centigrade.

GC-Ms Analysis:

Samples were analyzed using an HP6890 GC (Agilent Technologies, Palo Alto, Calif.) GC equipped with an HP-5973 mass detector and a DB column (JW Scientific (available through Fisher Scientific, Pittsburgh, Pa.).

NMR Analysis:

NMR spectra ware obtained on a Bruker DRX Advance (500 MHz $^1$H, 125 MHz $^{13}$C; Bruker Biospin in Corp., Billerica, Mass.) using deuterated solvents obtained from Cambridge Isotope Laboratories, Inc. (Andover, Mass.).

Example 1

Hydrogenation of Caryophyllene (50° C.)

An 18.5 wt % solution of caryophyllene (Sigma-Aldrich; St. Louis, Mo.; purchased as beta-caryophyllene) in absolute ethanol was prepared. GC-MS and NMR analysis of the caryophyllene indicated that it was a mixture of both the alpha- (13.31) and beta- (86.7%) isomers (MW 204).

This solution was hydrogenated using ESCAT-142 (Engelhard, Iselin, N.J.; 5% Pd/C powder catalyst) using 10% powdered catalyst by weight relative to the beta caryophellene; the reaction was carried out for 2 hours at 50° C. and 3.45 MPa hydrogen pressure. GC-MS and NMR analysis of the hydrogenated solution indicated that alpha-caryophyllene (alpha-humulene) was not hydrogenated, and beta-caryophyllene was converted to dihydro-β-caryophyllene.

Example 2

Hydrogenation of Caryophyllene (100 Degrees C.)

An 18.5% solution of caryophyllene (Sigma-Aldried) in absolute ethanol was prepared as described in Example 1.

This solution was hydrogenated using ESCAT-142 using 10% powdered catalyst by weight relative to the beta caryophellene; the reaction was carried out for 2 hours at 100 degrees C. and 3.45 MPa hydrogen pressure. GC-MS and NMR analysis of the hydrogenated solution indicated that alpha-humulene and beta-caryophyllene were completely hydrogenated to alpha-humulane and beta-caryophyllane, respectively.

Example 3

Hydrogenation of Caryophyllene

A 50 mL stirred batch autoclave reactor was charged with 31.41 g of a 50 wt % solution of caryophyllene (prepared as described in Example 1) and 1.59 g of ESCAT 142. The reactor was equipped with a magnetically-coupled gas entrainment agitator which was rotated at about 1000 rpm during the reaction. The reactor was scaled and then flushed and evacuated with nitrogen several times to remove oxygen. These flushes were followed by two rapid flushes with hydrogen to minimize residual nitrogen in the reactor. The reactor was heated to approximately 50 degrees C. via an external band heater and then charged to 83.9 bar (8.39 MPa) pressure with hydrogen. Hydrogen was continuously fed to the reactor during the course of the run to maintain this pressure as hydrogen was consumed by reaction.

Small samples of the reaction mixture were removed periodically via a dip tube equipped with a 2 micron sintered metal frit. The reactor was maintained at an average temperature of 54° C. for a total reaction time of 3.0 hours. The reactor was then thermally quenched via an external cooling coil supplied with a chilled propylene glycol/water mixture from a recirculating bath and vented. Product analysis by gas chromatography (GC-FID) using 1,2-dibromobenzene as an internal standard added post reaction showed 99.7% conversion of both caryophyllene isomers after 0.5 hours, and quantitative conversion by 1.10 hours reaction time. Additional analysis by mass spectroscopy (GC-MS) and $C^{13}$ NMR identified the anticipated hydrogenation product isomers for both the alpha- and beta-caryophyllene (humulane and caryophyllane, respectively). Concentrations of the pertinent reactants and reaction products are summarised in Table 1, and FIG. 1 plots the concentrations of the various isomers of each molecular weight. This example demonstrates complete and rapid hydrogenation of alpha- and beta-caryophyllene at commercially-viable reactor concentrations in the solvent (i.e. high reactor productivity).

TABLE 1

| Time on Stream (hr) | Beta-Caryo-phyllene (MW 204) (wt %) | Alpha-Caryo-phyllene (MW 204) (wt %) | Sum of MW 206 Isomers (wt %) | Sum of MW 208 Isomers (wt %) | Sum of MW 210 Isomers (Humulane) (wt %) |
|---|---|---|---|---|---|
| 0.00 | 84.50 | 7.82 | 0.21 | 0.02 | 0.07 |
| 0.17 | 1.56 | 1.91 | 75.13 | 5.53 | 0.79 |
| 0.50 | 0.08 | 0.20 | 41.73 | 39.06 | 5.75 |
| 1.10 | 0.04 | 0.02 | 10.89 | 68.03 | 9.69 |
| 1.50 | 0.03 | 0.02 | 3.16 | 75.48 | 10.51 |
| 2.10 | 0.02 | 0.02 | 0.83 | 80.06 | 11.92 |
| 2.50 | 0.02 | 0.02 | 0.60 | 81.42 | 11.75 |
| 3.00 | 0.02 | 0.02 | 0.56 | 81.48 | 11.66 |

Example 4

Hydrogenation of Caryophyllene in Catnip Oil

A 50 mL stirred batch autoclave reactor was charged with 34.6 g of a 50 wt % solution of catnip oil in absolute ethanol and 1.73 g of ESCAT 142. The catnip oil was obtained by steam distillation of catnip plants (George Thacker Sons Farm, Alberta, Canada, 2003), and this as-received, oil was azeotropically dried with isopropanol. The reactor was equipped with a magnetically-coupled gas entrainment agitator which was rotated at about 1000 rpm during the reaction. The reactor was sealed and then chilled to 15 degrees C. via an external cooling coil supplied with a chilled propylene glycol/water mixture from a recirculating bath. The reactor was flushed and evacuated with nitrogen several times to remove oxygen, and these flushes were followed by two rapid flushes with hydrogen to minimize residual nitrogen in the reactor. The reactor was charged to 86 bar (8.6 MPa) pressure with hydrogen. Hydrogen was continuously fed to the reactor during the course of the run to maintain this pressure as hydrogen was consumed by reaction.

Small samples of the reaction mixture were removed periodically via a dip tube equipped with a 2 micron sintered metal frit. The reactor was maintained at an average temperature of 15 degrees C. for a reaction time of 4 hours, then the reactor was heated to approximately 100 degrees C. via an external band heater for an additional 2 hours. The reactor was then thermally quenched via the external cooling coil and vented. Product analysis by gas chromatography (GC-FID) using 1,2-dibromobenzene as an internal standard added post reaction showed 97.6% conversion of both caryophyllene isomers alter 1.75 hours at 15 degrees C., and quantitative conversion by the end of the reaction at 100 degrees C. Additional analysis by mass spectroscopy (GC-MS) identified the anticipated hydrogenation product isomers for both the alpha- and beta-caryophyllene (humulane and caryophyllane, respectively). Concentrations of the pertinent reactants and reaction products are summarized in Table 2. This example demonstrates complete and rapid hydrogenation of alpha- and beta-caryophyllene as minor components of a natural product.

TABLE 2

| Time on Stream (hr) | Reactor Temp. (° C.) | Beta-Caryo-phyllene (MW 204) (wt %) | Alpha-Caryo-phyllene (MW 204) (wt %) | Sum of MW 208 Isomers (Caryo-phyllane) (wt %) | Sum of MW 210 Isomers (Humulane) (wt %) |
|---|---|---|---|---|---|
| 0.00 | 1.40 | 7.70 | 1.29 | — | — |
| 0.17 | 15.4 | 4.40 | 0.80 | 0.17 | 0.20 |
| 0.50 | 15.3 | 0.19 | 0.18 | 0.30 | 0.46 |
| 1.75 | 15.0 | 0.20 | 0.02 | 0.71 | 0.13 |
| 2.75 | 15.1 | 0.19 | 0.03 | 0.78 | 0.13 |
| 4.00 | 15.2 | 0.20 | 0.03 | 0.94 | 0.29 |
| 4.60 | 94.2 | 0.15 | 0.00 | 4.36 | 0.51 |
| 5.85 | 100.5 | 0.05 | 0.00 | 6.44 | 1.08 |

Where a range of numerical values is recited herein, the range includes the endpoints thereof and all the individual integers and fractions within the range, and also includes each of the narrower ranges therein formed by ail the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the contest of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a slated value of those values outside it that have, within the context of this invention, functional and/or operable equivalence to the stated value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

A catalyst suitable for use herein may be selected as any one or more or ail of the members of the whole population of catalysts described by name or structure above. A suitable catalyst may, however, also be selected as any one or more or all of the members of a subgroup of the whole population, where the subgroup may be any size (1, 2, 4 or 6, for example), and where the subgroup is formed by omitting any one or more of the members of the whole population as described above. As a result, the catalyst may in such instance not only be selected as one or more or all of the members of any subgroup of any size that may be formed from the whole population of catalysts as described above, but the catalyst may also be selected in the absence of the members that have been omitted from the whole population to form the subgroup. For example, in certain embodiments, the catalyst useful herein may be selected as one or more or all of the members of a subgroup of catalysts that excludes from the whole population ruthenium supported on titania, with or without the exclusion from the whole population, of other catalysts too.

What is claimed is:

1. A composition of matter or an article of manufacture comprising (a) dihydro-β-caryophyllene and at least one member of the group consisting of α-humulane and β-caryophyllane; (b) a dihydronepetalactone or derivative thereof; and (c) a sunscreening or sunblocking agent.

2. A composition or article according to claim 1 wherein a dihydronepetalactone comprises 1S,9S,5R,6R-5,9-dimethyl-3-oxabicyclo[4.3.0]nonan-2-one.

3. A composition according to claim 1 further comprising one or more members of the group of adjuvants consisting of thickeners, chelating agents, preservatives, stabilizers, surfactants.

4. A composition according to claim 1 that is fabricated in the form of a sprayable liquid, an aerosol, a foam, a cream, an ointment, a gel, a paste, a powder or a friable solid.

5. A composition according to claim 1 that further comprises one or more members of the group of adjuvants consisting of thickeners, chelating agents, preservatives, stabilizers, surfactants, and that is formulated as a lotion.

6. An article according to claim 1 that is fabricated as a member of the group consisting of a textile, fibrous goods, clothing, sanitary goods, carpeting, linens, outdoor equipment, military equipment, candles, paper, paint, ink, wood products, plastics and polymers.

7. An article according to claim 1 that is fabricated as mosquito netting.

* * * * *